United States Patent
Hatori (10) Patent No.: US 7,701,585 B2
(45) Date of Patent: Apr. 20, 2010

(54) OPTICAL TOMOGRAPH WHICH OBTAINS TOMOGRAPHIC IMAGES IRRESPECTIVE OF POLARIZATION DIRECTION OF LIGHT BEAMS

(75) Inventor: Masami Hatori, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 98 days.

(21) Appl. No.: 11/944,907

(22) Filed: Nov. 26, 2007

(65) Prior Publication Data
US 2008/0123092 A1 May 29, 2008

(30) Foreign Application Priority Data
Nov. 24, 2006 (JP) ............................. 2006-316613

(51) Int. Cl.
G01B 9/02 (2006.01)
G01B 11/02 (2006.01)

(52) U.S. Cl. .................... 356/479; 356/497; 356/495
(58) Field of Classification Search .................. 356/477, 356/479, 497, 485, 489, 492, 495
See application file for complete search history.

(56) References Cited

U.S. PATENT DOCUMENTS

| | | | | |
|---|---|---|---|---|
| 4,976,543 | A * | 12/1990 | Scheck et al. | ................ 356/624 |
| 5,028,134 | A | 7/1991 | Bulpitt et al. | |
| 6,208,415 | B1 * | 3/2001 | De Boer et al. | ............. 356/485 |
| 6,564,089 | B2 | 5/2003 | Izatt et al. | |
| 6,615,072 | B1 | 9/2003 | Izatt et al. | |
| 6,665,456 | B2 * | 12/2003 | Dave et al. | ................... 356/477 |
| 7,016,048 | B2 * | 3/2006 | Chen et al. | ................... 356/497 |
| 2005/0036150 | A1 * | 2/2005 | Izatt et al. | ................... 356/479 |
| 2006/0038999 | A1 | 2/2006 | Hentschel et al. | |
| 2006/0114471 | A1 | 6/2006 | Cyr | |
| 2006/0215170 | A1 | 9/2006 | Toida et al. | |
| 2006/0256348 | A1 | 11/2006 | Toida et al. | |
| 2007/0086017 | A1 | 4/2007 | Buckland et al. | |
| 2007/0236700 | A1 * | 10/2007 | Yun et al. | ................... 356/477 |

FOREIGN PATENT DOCUMENTS

| | | |
|---|---|---|
| EP | 1704814 A2 | 9/2006 |
| EP | 1704814 A3 | 9/2006 |

(Continued)

OTHER PUBLICATIONS

Todorović et al., Burn depth determination using high-speed polarization-sensitive Mueller optical coherence tomography with continuous polarization modulation, Proceedings of SPIE, vol. 6079, Feb. 15, 2006, pp. 60792B-1-60792B-5.

(Continued)

Primary Examiner—Patrick J Connolly
(74) Attorney, Agent, or Firm—Sughrue Mion, PLLC (57) ABSTRACT

An optical tomograph which irradiates and scans a measuring light beam onto a measurement target at a predetermined scanning frequency, to obtain a tomographic image of the measurement target is provided. A depolarizing unit, for varying the polarization state of light beams input thereto at a frequency equivalent to or higher than the scanning frequency, such that the light beam output therefrom becomes depolarized when averaged over time, is provided in the optical path of at least one of the measuring light beam, a reference light beam, and a reflected light beam between a light source unit and a combining unit.

19 Claims, 8 Drawing Sheets

FOREIGN PATENT DOCUMENTS

| | | |
|---|---|---|
| EP | 1705476 A1 | 9/2006 |
| JP | 06-147905 | 5/1994 |
| JP | 2001-264246 A | 9/2001 |

OTHER PUBLICATIONS

Jiao et al., Fiber-based polarization-sensitive Mueller matrix optical coherence tomography with continuous source polarization modulation, Applied Optics, vol. 44, No. 26, Sep. 10, 2005, pp. 5463-5467.

Kersey et al., Analysis of Input-Polarization-Induced Phase Noise in Interferometric Fiber-Optic Sensors and Its Reduction using Polarization Scrambling, Journal of Lightwave Technology, vol. 8, No. 6, Jun. 1, 1990, pp. 838-845.

Mitsuo Takeda, "Optical Frequency Scanning Interference Microscopes", Optics Engineering Contact, 2003, pp. 426-432, vol. 41, No. 7.

* cited by examiner

OPTICAL TOMOGRAPH WHICH OBTAINS TOMOGRAPHIC IMAGES IRRESPECTIVE OF POLARIZATION DIRECTION OF LIGHT BEAMS

BACKGROUND OF THE INVENTION

1. Field of the Invention

The present invention relates to an optical tomograph that obtains optical tomographic images by OCT (Optical Coherence Tomography) measurement.

2. Description of the Related Art

Conventionally, optical tomographs that utilize OCT measurement are employed to obtain tomographic images of living tissue. In an optical tomograph, a low coherence light beam emitted from a light source is divided into a measuring light beam and a reference light beam. Thereafter, a reflected light beam, which is the measuring light beam reflected by a measurement target when the measuring light beam is irradiated onto the measurement target, is combined with the reference light beam. Tomographic images are obtained, based on the intensity of a interference light beam obtained by combining the reflected light beam and the reference light beam (refer to U.S. Pat. Nos. 6,564,089 and 6,615,072, and Japanese Unexamined Patent Publication No. 2001-264246, for example).

OCT measurement can be roughly divided into two types, TD-OCT (Time Domain Optical Coherence Tomography) and FD-OCT (Fourier Domain Optical Coherence Tomography). In TD-OCT measurement, the intensity of the interference light beam is measured while changing the optical path length of the reference light beam. Thereby, intensity distributions of the reflected light beam corresponding to measuring positions in the depth direction of the measurement target (hereinafter, referred to as "depth positions") are obtained.

On the other hand, in FD-OCT measurement, the optical path lengths of the reference light beam and the signal light beam are not changed. The intensity of the interference light beam is measured for each spectral component thereof, and frequency analysis, such as Fourier transform, is administered on the obtained spectral interference intensity signals. Thereby, intensity distributions of the reflected light beam corresponding to the depth positions of the measurement target are obtained. FD-OCT measurement has been gathering attention recently as a method that enables high speed measurement, due to the mechanical scanning associated with TD-OCT measurement being obviated.

Optical tomographs that perform SD-OCT (Spectral Domain Optical Coherence Tomography) measurement and optical tomographs that perform SS-OCT (Swept Source Optical Coherence Tomography) measurement are two types of optical tomographs that employ FD-OCT measurement. In an SD-OCT optical tomograph, a wide band low coherence light beam is emitted from an SLD (Super Luminescent Diode), an ASE (Amplified Spontaneous Emission) light source, or a white light source. The wide band low coherence light beam is divided into a measuring light beam and a reference light beam by a Michelson interferometer or the like. Thereafter, the measuring light beam is irradiated onto a measurement target, and a reflected light beam reflected by the measurement target is caused to interfere with the reference light beam. The interference light beam formed thereby is spectrally decomposed into each frequency component by a spectrometer, and the intensity of each frequency component of the interference light beam is measured by a detector array, in which elements such as photodiodes are provided in an array. A computer administers Fourier transform on the obtained spectral interference intensity signals, to obtain a tomographic image.

Meanwhile, an SS-OCT optical tomographs utilizes a light source that periodically sweeps the frequency of a laser beam. Reflected light beams of each wavelength are caused to interfere with reference light beams of each wavelength. Temporal waveforms of signals corresponding to the temporal variations in the frequency of the laser beam are measured, and a computer administers Fourier transform on the obtained spectral interference intensity signals, to obtain a tomographic image.

It is common for the various types of optical tomographs described above to employ lasers as light sources, and to employ optical fibers as optical waveguide means. Particularly when the optical tomographs are applied to endoscopes, it is common for optical fibers to be employed to guide light into body cavities.

During insertion of optical fibers into body cavities and during measurement, bending and twisting of the optical fibers occurs, as well as temperature changes due to insertion into the body cavities. Single mode fibers, which are generally employed in endoscopes, cannot preserve polarized states during propagation of light therethrough. Therefore, when forces such as bending and twisting, or variation factors such as temperature change and vibration are applied, the birefringent properties of the optical fibers varies irregularly.

In OCT measurement, an interference light beams is generated by combining a reflected light beam with a reference light beam. The intensity of the interference light beam varies according to the polarization directions of the reflected light beam and the reference light beam. The intensity of the interference light beam becomes maximal when the polarization directions of the reflected light beam and the reference light beam match. As described above, however, if the birefringent properties of the optical fibers varies, the polarization direction of the reflected light beam or the reference light beam also varies, resulting in variations in the intensity of the interference light beam. These intensity variations become fluctuations in interference signal levels, which causes density stripes to be generated in a tomographic image, thereby decreasing the image quality thereof. Depending on the degree of image quality deterioration, targets of diagnosis which should be discriminated may be overlooked.

The optical tomographs disclosed in U.S. Pat. Nos. 6,564, 089 and 6,615,072 are provided with Faraday rotators at the tips of probes thereof, to compensate for variations in interference intensity due to birefringent changes caused by bending of an optical fiber. Magnetic garnet monocrystals, in which the crystal itself has magnetism, are employed as the material of the Faraday rotator. However, this type of Faraday rotator is likely to generate ghosts due to reflection, because the refractive index of the magnetic body is high. For this reason, reflection preventing measures, such as provision of a watertight seal filled with index matching fluid, forming bonding surfaces at angles other than right angles to prevent feedback of reflected light, and the like, become necessary. The reflection preventing measures lead to increases in manufacturing costs.

In addition, U.S. Pat. Nos. 6,564,089 and 6,615,072 disclose that it is important to employ polarization controllers that match the polarization direction of a light beam reflected by a measurement target and the polarization direction of a reference light beam, to cause the intensity of a interference light beam formed by interference of these two light beams to become maximal. However, in tomographs that employ the aforementioned polarization controllers, operating speeds are slow, because the polarization controllers are mechanically driven. Another shortcoming is that it takes time to find optimal combinations of operational parameters, as there are three parameters to be adjusted. Regarding adjustment by polarization controllers, there is the aforementioned problem of control speed thereof. Therefore, if the polarization direction shifts greatly during diagnosis utilizing OCT measurement, there is a possibility that diagnosis will be interrupted.

SUMMARY OF THE INVENTION

The present invention has been developed in view of the foregoing circumstances. It is an object of the present invention to provide a low cost optical tomograph that enables obtainment of tomographic images having high image quality, without adjusting the polarization directions of light beams.

An optical tomograph of the present invention comprises:

a light source unit for emitting a light beam;

light dividing means, for dividing the light beam emitted from the light source unit into a measuring light beam and a reference light beam;

scanning means, for scanning and irradiating the measuring light beam onto a measurement target at a predetermined scanning frequency;

combining means, for combining a reflected light beam, which is the measuring light beam reflected by the measurement target when scanned thereon, and the reference light beam;

interference light detecting means, for detecting an interference light beam, which is formed by the reflected light beam and the reference light beam being combined by the combining means; and image obtaining means, for detecting the intensity of the reflected light beam at a plurality of depth positions within the measurement target, based on the wavelength and intensity of the interference light beam detected by the interference light detecting means, and obtaining a tomographic image of the measurement target based on the intensities of the reflected light beam; characterized by further comprising:

depolarizing means, for varying the polarization state of light beams input thereto at a frequency equivalent to or higher than the scanning frequency, such that the light beam output therefrom becomes depolarized when averaged over time, provided in at least one of the following locations: within the light source unit; along the optical path of the light beam emitted from the light source unit between the light source unit and the combining means; along the optical path of the measuring light beam; along the optical path of the reference light beam; and along the optical path of the reflected light beam.

Here, the "scanning frequency" is based on the number of frames of tomographic images which are obtained within a single second. For example, in the case that f frames are obtained per second, the scanning frequency is f. The phrase "equivalent to the scanning frequency" refers to a frequency within a range of ±10% of the scanning frequency.

Here, the manner in which the depolarizing means varies the polarization state such that "the light beam output therefrom becomes depolarized when averaged over time" may be that in which the polarization direction is rotated 360 degrees regularly at high speed, or that in which random polarization states are irregularly generated within short periods. It becomes possible to reduce density stripes in resulting tomographic images, by varying the polarization state in this manner. In order to further reduce the density stripes in tomographic images, it is preferable for the polarization state to be varied at higher frequencies. Particularly, in the case that the polarization direction is swept and varied in a regular manner, it is preferable for the sweeping frequency of the polarization direction to be significantly higher than the scanning frequency. It is preferable for the polarization direction to be varied at a frequency 20 times the scanning frequency or higher.

The optical tomograph of the present invention may be configured such that: the light source unit emits a laser beam, of which the wavelength is swept with a predetermined sweeping frequency $f\lambda$; and the image obtaining means obtains the tomographic image of the measurement target by administering spectral analysis on the interference light beam. In this case, the depolarizing means varies the polarized state of the light beam input thereto at a frequency equivalent to or higher than the sweeping frequency $f\lambda$. Here, the phrase "a frequency equivalent to the sweeping frequency $f\lambda$" refers to a frequency within a range of ±10% of the sweeping frequency $f\lambda$.

Further, the optical tomograph of the present invention may be configured such that the depolarizing means varies the polarized state of the light beam input thereto at a frequency equivalent to or higher than $N \times f\lambda$, wherein N is the number of depth positions at which the intensity of the reflected light beam is detected, and $f\lambda$ is the frequency at which the wavelength of the laser beam is swept. Here, the phrase "a frequency equivalent to $N \times f\lambda$" refers to a frequency within a range of ±10% of the product $N \times f\lambda$.

Alternatively, the optical tomograph of the present invention may be configured such that the light source unit emits low coherence light; and the image obtaining means obtains the tomographic image of the measurement target by administering spectral analysis on the interference light beam.

The depolarizing means may comprise: a wavelength plate provided in the optical path of the light beam input into the depolarizing means; and drive means, for rotating the wavelength plate about the optical axis of the light beam, or for vibrating the wavelength plate. A ½ wavelength plate that rotates the polarization direction of a linearly polarized input light beam may be employed.

Alternatively, the depolarizing means may comprise: an optical fiber that constitutes the optical path of at least one of the light beam emitted by the light source unit, the measuring light beam, the reference light beam, and the reflected light beam, between the light source unit and the combining means; and force applying means, for applying force on the optical fiber.

The optical tomograph of the present invention comprises the depolarizing means, for varying the polarization state of light beams input thereto at a frequency equivalent to or higher than the scanning frequency, such that the light beam output therefrom becomes depolarized when averaged over time. Therefore, the polarization state of the light can be caused to approach a depolarized state more than in a case that the depolarizing means is not provided. Accordingly, density stripes in resulting tomographic images can be reduced, and tomographic images having high image quality can be obtained without adjusting the polarization directions of light beams. In addition, there is a greater degree of freedom in the placement of the depolarizing means of the present invention compared to a conventional magnetic Faraday rotator, which is provided at the tip of a probe. Further, the depolarizing means can be realized with a simple construction, and therefore the optical tomograph can be manufactured at low cost.

The optical tomograph of the present invention may be configured such that: the light source unit emits a laser beam, of which the wavelength is swept with a predetermined sweeping frequency $f_\lambda$; and the image obtaining means obtains the tomographic image of the measurement target by administering spectral analysis on the interference light beam; and the depolarizing means varies the polarized state of the light beam input thereto at a frequency equivalent to or higher than the sweeping frequency $f_\lambda$. In this case, tomographic images having high image quality can be obtained without adjusting the polarization directions of light beams during measurements for each sweeping operation in SS-OCT measurement, at low cost.

Further, the optical tomograph of the present invention may be configured such that the depolarizing means varies the polarized state of the light beam input thereto at a frequency equivalent to or higher than $N \times f_\lambda$, wherein N is the number of depth positions at which the intensity of the reflected light beam is detected, and $f_\lambda$ is the frequency at which the wavelength of the laser beam is swept. In this case, tomographic images having high image quality can be obtained without adjusting the polarization directions of light beams during measurements of each depth position in SS-OCT measurement, at low cost.

Alternatively, the optical tomograph of the present invention may be configured such that the light source unit emits low coherence light; and the image obtaining means obtains the tomographic image of the measurement target by administering spectral analysis on the interference light beam. In this case, tomographic images having high image quality can be obtained without adjusting the polarization directions of light beams in SD-OCT measurement, at low cost.

DESCRIPTION OF THE PREFERRED EMBODIMENTS

Hereinafter, optical tomographs according to embodiments of the present invention will be described hereinafter, with reference to the attached drawings.

Figure 1:
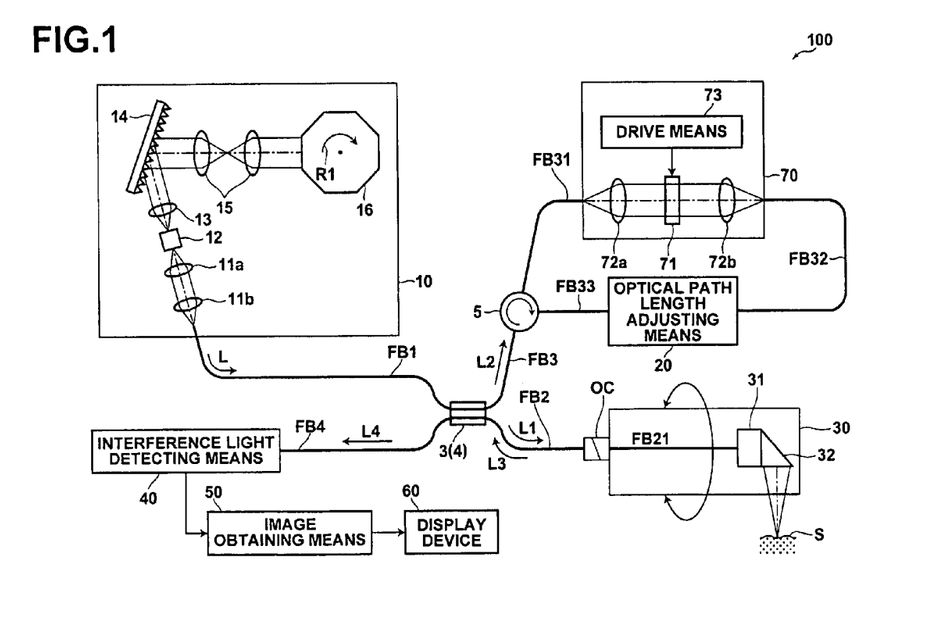
FIG. 1 is a diagram that illustrates the construction of an optical tomograph according to a first embodiment of the present invention.

FIG. 1 is a diagram that illustrates the construction of an optical tomograph 100 according to the first embodiment of the present invention. The optical tomograph 100 obtains tomographic images of measurement targets, such as living tissue and cells within body cavities, by SS-OCT measurement.

The optical tomograph 100 comprises: a light source unit 10, for emitting a light beam L; a light dividing means 3, for dividing the light beam L emitted from the light source unit 10 into a measuring light beam L1 and a reference light beam L2; an optical path length adjusting means 20, for adjusting the optical path length of the reference light beam L2 output by the light dividing means 3; a probe 30, for scanning the measuring light beam L1 output by the light dividing means 3 on a measurement target S at a predetermined scanning frequency; a combining means 4, for combining a reflected light beam L3, which is the measuring light beam L1 reflected by the measurement target S, and the reference light beam L2; an interference light detecting means 40, for detecting a interference light beam L4, which is the reflected light beam L3 and the reference light beam L2 which are combined by the combining means 4; an image obtaining means 50, for detecting the intensity of the reflected light beam L3 at a plurality of depth positions within the measurement target S, based on the wavelength and intensity of the interference light beam L4 detected by the interference light detecting means 40, and obtaining a tomographic image of the measurement target S based on the intensities of the reflected light beam L3; and a depolarizing means 70, for varying the polarization state of light beams input thereto at a frequency equivalent to or higher than the scanning frequency, such that the light beam output therefrom becomes depolarized when averaged over time.

An optical fiber FB1 is provided to guide the light beam L between the light source unit 10 and the light dividing means 3. An optical fiber FB2 is provided to guide the measuring light beam L1 and the reflected light beam L3 between the light dividing means 3 and the probe 30. An optical fiber FB21 is provided to guide the measuring light beam L1 and the reflected light beam L3 within the probe 30. An optical fiber FB4 is provided to guide the interference light beam L4 between the combining means 4 and the interference light detecting means 40. Optical fibers FB3, FB31, FB32, and FB33 are provided to guide the reference light beam L2 between the light dividing means 3 and a circulator 5, between the circulator 5 and the depolarizing means 70, between the depolarizing means 70 and the optical path adjusting means 20, and between the optical path adjusting means 20 and the circulator 5, respectively. The optical fibers FB1, FB2, FB21, FB3, FB31, FB32, FB33, and FB4 are all polarization independent single mode fibers.

The light source unit 10 emits a laser beam as the light beam L, while sweeping the frequency thereof at a predetermined sweeping frequency $f_\lambda$. A semiconductor medium, which is used for semiconductor lasers, is utilized as the laser medium. Specifically, the light source unit 10 comprises: optical linking lenses 11a and 11b; a semiconductor laser medium 12; a collimating lens 13; a diffracting optical element 14; relay lenses 15; and a polygon mirror 16.

The collimating lens 13 collimates the light beam emitted from the semiconductor laser medium 12. The wavelengths of the collimated light beam are spatially dispersed by the diffracting optical element 14. The light beam passes through the relay lenses 15, and is reflected by the polygon mirror 15. A portion of the reflected light beam passes through the same path in the reverse direction, and returns to the semiconductor laser medium as a feedback light beam.

The polygon mirror 16 rotates in the direction indicated by arrow R1, to vary the angle of each reflective surface thereof with respect to the optical axis of the relay lenses 15. Thereby, only a light beam having a specific wavelength, from among the light beam of which the wavelengths have been spatially dispersed by the diffraction grating 14, returns to the semiconductor laser medium 12 as the feedback light beam. A resonator is constituted by the light emitting facet of the semiconductor laser medium 12 toward the side of the collimating lens 13 and the polygon mirror 16. The laser light beam L is emitted from the light emitting facet of the semiconductor laser medium 12 toward the side of the optical coupling lens 11a. Note that the wavelength of the laser beam L is determined by the wavelength of the feedback light beam. The laser light beam L which is emitted by the semiconductor laser medium 12 is collimated by the lens 11a, focused by the lens 11b, and enters the optical fiber FB1.

The wavelength of the feedback light beam is determined by the angle between the optical axis of the relay lenses 15 and the reflective surface of the polygon mirror 16. Therefore, as the polygon mirror 16 rotates in the direction of the arrow R1 at a constant speed, the wavelength of the light beam that reenters the semiconductor laser medium 12 from the polygon mirror 16 changes with a predetermined period over the passage of time. As a result, the laser beam L having a wavelength which is swept at the predetermined period is emitted from the light source unit 10 into the optical fiber FB1.

The light dividing means 3 is constituted by a 2×2 optical fiber coupler, for example. The light dividing means 3 functions to divide the light beam L emitted by the light source unit 10 and guided through the optical fiber FB1 into the measuring light beam L1 and the reference light beam L2. The light dividing means 3 is optically connected to the optical fibers FB2 and FB3. The measuring light beam L1 is guided through the optical fiber FB2, and the reference light beam L2 is guided through the optical fiber FB3. Note that the light dividing means 3 of the present embodiment also functions as the combining means 4.

The optical fiber FB2 is optically connected to the probe 30 via an optical rotary connector OC, and the measuring light beam L1 is guided through the optical fiber FB2 to the probe 30. The probe 30 is to be inserted into body cavities via a forceps opening and a forceps channel, in the case that the optical tomograph 100 is applied to an endoscope. The probe 30 comprises: a probe outer cylinder, which has a closed distal end; the optical fiber FB21, which is provided to extend along the axial direction of the outer cylinder within the interior space thereof, for guiding the measuring light beam L1 and the reflected light beam L3; a gradient index lens 31, for focusing the measuring light beam L1 emitted from the tip of the optical fiber FB21 such that it converges within the measurement target S; and a reflective prism 32, for reflecting the measuring light beam L1, which has passed through the gradient index lens 31, toward the measurement target S.

The probe 30 is configured such that the optical fiber FB21, the gradient index lens 31 and the reflective prism 32 can be rotated with respect to the optical rotary connector OC by a motor (not shown). The measuring light beam emitted from the probe 30 is scanned in the circumferential direction of the probe by this rotation, at the predetermined scanning frequency. This scanning enables obtainment of two dimensional tomographic images. Further, a motor (not shown) is configured to scan the distal end of the probe 30 in the longitudinal direction of the optical fiber FB21. Thereby, obtainment of three dimensional tomographic images is also enabled.

Note that the amount of light loss at the optical rotary connector OC is set to be almost 0 during the rotation in the circumferential direction. In addition, the probe 30 is removably mounted to the optical fiber FB2 via an optical connector (not shown). Of course, the shape of the distal end of the probe 30 and the scanning method are not limited to those described above. Alternatively, two dimensional scanning may be realized by providing a high speed scanning mirror at the distal end of the probe 30, for example.

Meanwhile, the circulator 5, the depolarizing means 70, and the optical path length adjusting means 20 are provided in this order along the optical path of the reference light beam L2 beyond the optical fiber FB3. The depolarizing means 70 rotates the polarization direction of the reference light beam L2 at high speed, to create a state equivalent to that in which a non polarized reference light beam is employed, to reduce density stripes in tomographic images.

The depolarizing means 70 comprises: a ½ wavelength plate 71, provided along the optical path of the reference light beam L2; optical linking lenses 72a and 72b, provided on each side of the ½ wavelength plate 71 in the optical axis direction of the reference light beam L2; and a drive means 73, for rotating the ½ wavelength plate 71 about the optical axis of the reference light beam L2. Note that in the present embodiment, the drive means 73 rotates the ½ wavelength plate 71. However, the present invention is not limited to this configuration, and the drive means 73 may alternatively vibrate the ½ wavelength plate 71.

The ½ wavelength plate 71 functions to rotate the polarization direction of linearly polarized light. If ½ wavelength plates are rotated by an angle of $\theta$, linearly polarized light beams incident thereon are emitted as linearly polarized light beams having polarization directions rotated $2\theta$ from their original polarization directions.

The reference light beam L2 emitted from the optical fiber 31 is input to the depolarization means 70, collimated by the lens 72a, then converted into a light beam of which the polarization direction is rotated at high speed when it passes through the ½ wavelength plate, focused by the lens 72, and output into the optical fiber FB32.

At this time, the drive means 73 rotates the ½ wavelength plate such that the polarization direction of the reference light beam L2 output from the depolarizing means 70 is rotated at a frequency equivalent to or higher than the scanning frequency. Preferably, the rotating frequency is significantly higher than the scanning frequency, such as 20 times the scanning frequency. In the optical tomograph 100 having the construction described above, an image obtained by a single rotation of the optical fiber FB21 within the probe 30 corresponds to a single frame. In a common optical tomograph, the optical fiber FB21 rotates 10 to 20 times per second. That is, the scanning frequency is 10 Hz to 20 Hz.

Therefore, as a specific example, in the case that the scanning frequency is 10 Hz to 20 Hz, the ½ wavelength plate is rotated at a frequency higher than 10 Hz to 20 Hz, and preferably at a frequency of 100 Hz to 1 kHz. To simplify the explanation, assume that a linearly polarized light beam is input to the depolarizing means 70. Because the polarization direction of the light beam rotates $2\theta$ when the ½ wavelength plate 71 is rotated by an angle of $\theta$ as described above, a light beam, of which the polarization direction rotates at 200 Hz to 2 kHz, is output from the depolarizing means 70, if the ½ wavelength plate 71 is rotated at 100 Hz to 1 kHz. That is, the polarization direction of the reference light beam L2 is swept and rotated 10 to 200 times during obtainment of a single frame of a tomographic image. In the case that the polarization direction is varied at such a frequency, which is significantly higher than the scanning frequency, the results averaged over time are practically the same as those obtained when a non polarized light beam is employed. Therefore, density stripes within the tomographic image can be greatly reduced. Note that if the polarization direction is varied at a frequency equivalent to the scanning frequency, the effects of depolarization will be lower than those obtained by varying the polarization direction at a frequency significantly higher than the scanning frequency. However, density stripes can be reduced compared to a case in which the depolarizing means is not employed.

The optical path length adjusting means 20 functions to change the optical path length of the reference light beam L2, to adjust the initial position at which tomographic images of the measurement target S are obtained. The example illustrated in FIG. 1 is an optical path length adjusting means of the light transmissive type. Known light transmissive optical path adjusting means, such as that comprising a wedge shaped prism and a diffracting optical element as disclosed in Japanese Unexamined Patent Publication No. 2001-264246, may be employed.

Note that in the present embodiment, an optical tomograph comprising the depolarizing means employing the ½ wavelength plate and the optical path length adjusting means of the light transmissive type is described. However, the present invention is not limited to this configuration, and depolarizing means employing other types of wavelength plates may be used. In addition, an optical path length adjusting means of the reflective type may be used, depending on the type of wavelength plate which is employed in the depolarizing means.

The combining means 4 is constituted by the aforementioned 2×2 optical coupler. The combining means 4 combines the reference light beam L2, which propagates thereto after passing through the depolarizing means 70 and the optical path length adjusting means 20, and the reflected light beam L3 reflected by the measurement target S. The combined interference light beam L4 is emitted toward the interference light detecting means 40 via the optical fiber FB4, which is provided to guide the interference light beam L4.

The interference light detecting means 40 detects the interference light beam L4 formed by the combining means 4 combining the reflected light beam L3 and the reference light beam L2, and measures the intensity thereof. The interference light detecting means 40 is connected to the image obtaining means 50, which is constituted by a computer system such as a personal computer. The image obtaining means 50 is connected to a display device 60, which is constituted by a CRT (Cathode Ray Tube), a liquid crystal display, or the like. The image obtaining means 50 obtains tomographic images of the measurement target S, by detecting the intensity of the reflected light beam L3 at various depth positions via spectral analysis of the interference light beam L4 detected by the interference light detecting means 40. The obtained tomographic images are displayed by the display device 60.

Here, detection of the interference light beam L4 by the interference light detecting means 40 and image generation by the image obtaining means 50 will be described briefly. Note that a detailed description of these two points can be found in M. Takeda, "Optical Frequency Scanning Interference Microscopes", Optical Technology Contact, Vol. 41, No. 7, pp. 426-432, 2003.

When the measuring light beam L1 is irradiated onto the measurement target S, the reflected light beam L3, which is reflected at various depths within the measurement target S and the reference light beam L2 interfere with each other, with various optical path length differences. By designating the optical intensity of the interference pattern with respect to each of the optical path length differences l as S(l), the optical intensity I(k) detected by the interference light detecting means 40 can be expressed as:

$$I(k) = \int_0^\infty S(l)[1+\cos(kl)]dl \qquad (1)$$

wherein:
  k: wave number
  l: optical path length difference

Formula (1) above may be considered as being provided as an interferogram of an optical frequency range, in which the wave number k=ω/c is a variable. For this reason, the image obtaining means 50 performs spectral analysis by administering Fourier transform on the spectral interference pattern detected by the interference light detecting means 40, to determine the optical intensity (I) of the interference light beam L4. Thereby, data regarding the intensity of the reflected light beam L3 at various depth positions within the measurement target S can be obtained, and generation of tomographic images is enabled. The display device 60 displays the generated tomographic images.

Hereinafter, the operation of the optical tomograph 100 having the above construction will be described. When obtaining a tomographic image, first, the optical path length adjusting means 20 adjusts the optical path length such that the measurement target S is positioned within a measurable region. Then, the drive means 73 of the depolarizing means 70 causes the ½ wavelength plate 71 to rotate at high speed. Thereafter, the light beam L is emitted from the light source unit 10. The light beam L is divided into the measuring light beam L1 and the reference light beam L2 by the light dividing means 3. The measuring light beam L1 is guided within a body cavity by the probe 30, and scanned and irradiated on the measurement target S at the predetermined scanning frequency. The reflected light beam L3, which is reflected by the measurement target S, propagates through the optical path of the measuring light beam L1 in reverse, and enters the combining means 4.

Meanwhile, the reference light beam L2 is converted to a light beam, of which the polarization state is varied at high speed, and enters the combining means 4 via the optical path length adjusting means 20. The combining means 4 combines the reflected light beam L3 and the reference light beam L2, and the interference light beam formed thereby is detected by the interference light detecting means 40. The signals representing the detected interference light beam L4 are spectrally analyzed by the image obtaining means 50, and a tomographic image is obtained.

As described above, the optical tomograph 100 comprises the depolarizing means 70. Therefore, the reference light beam L2 can be made to approach a depolarized state compared to a case in which the depolarizing means 70 is not provided. Accordingly, density stripes in obtained tomographic images can be reduced, and high quality tomographic images can be obtained. Particularly in the case that the depolarizing means 70 varies the polarization direction at a frequency significantly higher than the scanning frequency, density stripes only appear in tomographic images as high frequency differences in density, and are not visually recognized as stripes. That is, the image quality is substantially improved.

Compared to conventional methods, in which the polarizations directions of the reflected light beam and the reference light beam were adjusted to match each other, the amount of light contributed to interference is low in the optical tomograph 100. Consequently, the output intensity of the interference signals decreases. However, measurement is not interrupted for adjustments, and high quality tomographic images can be obtained continuously. In addition, the depolarizing means 70 can be of a simple structure as described above. That is, mechanisms for performing stringent adjustments are obviated, and therefore the tomograph can be constructed at low cost.

Commonly, optical components such as mirrors and fiber couplers have polarization properties, and the transmissivity, reflectance, division ratios and the like thereof differ, depending on the polarization direction of light beams incident thereon. In the optical tomograph 100, however, the reference light beam L2 is caused to become a non polarized light beam when averaged over time. Therefore, the influence of the polarization properties of the optical components can also be suppressed.

Note that in SS-OCT measurement, it is preferable for the depolarizing means to perform the variation in polarization state at a frequency equivalent to or higher than the wavelength sweeping frequency $f_\lambda$ of the laser beam or greater. For example, the polarization direction may be varied at a frequency 10 times or greater than the wavelength sweeping frequency $f_\lambda$. The wavelength sweeping frequencies $f_\lambda$ of laser beams in common SS-OCT measurement is from several Hz to several tens of kHz. In the case that fluctuations in polarization occur during the sweeping periods, it is preferable for the variation in polarization direction to be performed at a frequency equivalent to or higher than the wavelength sweeping frequency. This applies to SS-OCT measurement in general, and is not limited to the present embodiment.

Further, in SS-OCT measurement, taking the number N of depth positions within the measurement target S at which the intensity of the reflected light beam is detected into consideration, it is preferable for the polarization state to be varied at a frequency equivalent to or higher than $N \times f_\lambda$, for example, a frequency greater than or equal to $2 \times N \times f_\lambda$. Fine fluctuations greater than or equal to the number of image resolution points in the depth direction are not likely to be observed as deteriorations in image quality. Therefore, it is considered that varying the polarization state at a frequency of $2 \times N \times f_\lambda$ or greater is sufficiently effective. As a specific example, in the case that the wavelength sweeping frequency $f_\lambda$ is several Hz to several tens of kHz and N is 1000, it I preferable for the polarization state to be varied at a frequency of several kHz to several tens of MHz, in order to reduce density stripes in tomographic images. This applies to SS-OCT measurement in general, and is not limited to the present embodiment.

In all of the following embodiments to be described below, the depolarizing means thereof are assumed to vary the polarization state of light beams at a frequency equivalent to or higher than the scanning frequency of the measuring light beam.

Figure 2:
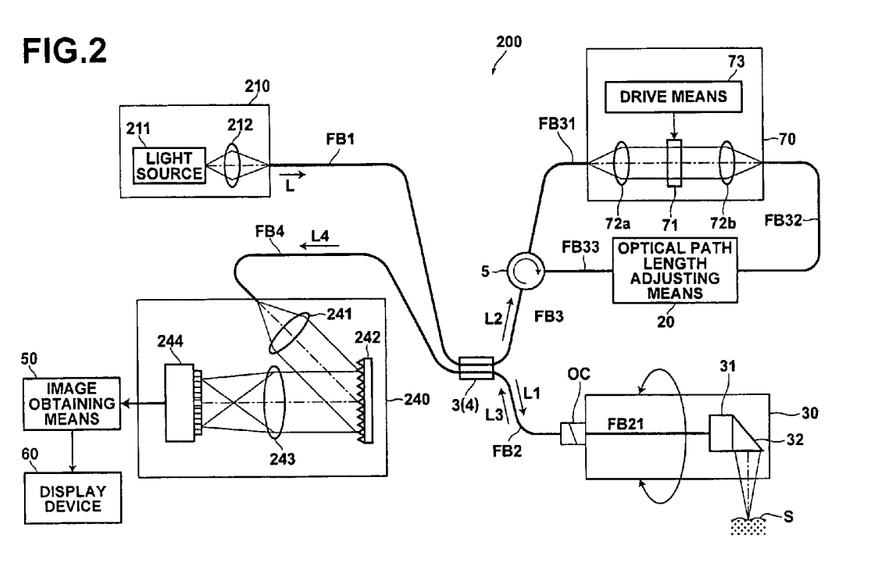
FIG. 2 is a diagram that illustrates the construction of an optical tomograph according to a second embodiment of the present invention.

Next, an optical tomograph 200 according to a second embodiment of the present invention will be described with reference to FIG. 2. Note that the optical tomograph 200 of the second embodiment is an SD-OCT apparatus that obtains tomographic images by SD-OCT measurement. The optical tomograph 200 differs from the optical tomograph 100 illustrated in FIG. 1 in the structures of the light source unit and the interference light detecting means. Components of the optical tomograph 200 illustrated in FIG. 2 which are the same as those of the optical tomograph 100 illustrated in FIG. 1 will be denoted with the same reference numerals, and detailed descriptions thereof will be omitted.

A light source unit 210 of the optical tomograph 200 comprises: a light source 211 that emits a low coherence light beam, such as an SLD (Super Luminescent Diode) or an ASE (Amplified Spontaneous Emission); and an optical system 212 that causes the light beam emitted from the light source 211 to enter the optical fiber FB1. Note that in the case that the optical tomograph 200 obtains tomographic images of measurement targets S, which are living tissue within body cavities, it is preferable to employ a short pulse laser light source that emits light within a wide spectral bandwidth, so that attenuation of the light beam due to scattering and absorption as it passes through the measurement target S can be minimized.

Meanwhile, an interference light detecting means 240 detects the interference light beam L4, formed by the combining means 4 combining the reflected light beam L3 and the reference light beam L2. The interference light detecting means 240 comprises: a spectral decomposing means 242, for decomposing the interference light beam L4 into each of its constituent wavelength bands; and a photodetecting means 244, for detecting each wavelength band of the interference light beam L4. The spectral decomposing means 242 is constituted by a diffraction optical element or the like. The spectral decomposing means 242 decomposes the interference light beam L4 incident thereon via a collimating lens 241, and sends the decomposed components toward the photodetecting means 244.

The photodetecting means 244 is constituted by optical sensors such as CCD elements, which are arranged one dimensionally or two dimensionally. Each of the optical sensors is configured to detect each wavelength band component of the spectrally decomposed interference light beam L4, incident thereon via an optical lens 243. Here, the interference light beam L4, in which Fourier transformed functions of reflective data are added to the spectrum of the light source unit 210, is observed. The image obtaining means 50 performs spectral analysis on the interference light beam L4 detected by the interference light detecting means 40, to obtain reflective data at various depth positions within the measurement target S, and to generate tomographic images. The display device 60 displays the generated tomographic images.

In the optical tomograph 200 of the second embodiment as well, the depolarizing means 70 is provided along the optical path of the reference light beam L2. Accordingly, the same advantageous effects as those obtained by the optical tomograph 100 of the first embodiment can be obtained. That is, an optical tomograph that obtains high quality tomographic images without adjusting the polarization directions of light beams can be obtained at low cost.

Figure 3:
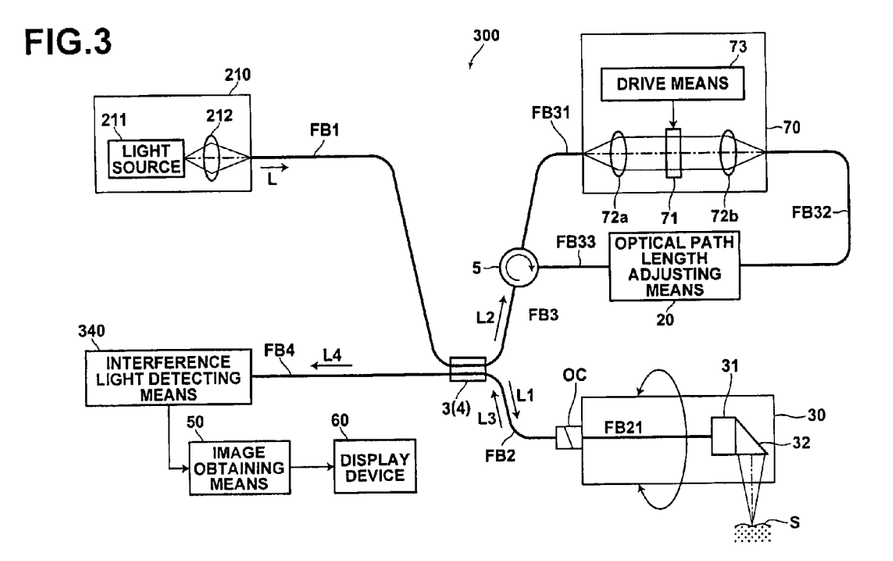
FIG. 3 is a diagram that illustrates the construction of an optical tomograph according to a third embodiment of the present invention.

Next, an optical tomograph 300 according to a third embodiment of the present invention will be described with reference to FIG. 3. Note that the optical tomograph 300 of the third embodiment is a TD-OCT apparatus that obtains tomographic images by TD-OCT measurement. The optical tomograph 300 differs from the optical tomograph 200 illustrated in FIG. 2 in the functions of the optical path length adjusting means and the interference light detecting means. Components of the optical tomograph 300 illustrated in FIG. 3 which are the same as those of the optical tomograph 200 illustrated in FIG. 2 will be denoted with the same reference numerals, and detailed descriptions thereof will be omitted.

The optical path length adjusting means 20 of the optical tomograph 300 functions to change the optical path length of the reference light beam L2, in order to vary measuring positions within the measurement target S in the depth direction thereof. Note that a phase modulator may be provided along the optical path of the reference light beam L2, to slightly shift the frequency of the reference light beam L2.

An interference light detecting means 340 of the optical tomograph 300 detects the intensity of the interference light beam L4 by heterodyne detection, for example. Specifically, if the sum of the optical path lengths of the measuring light beam L1 and the reflected light beam L3 is equal to the optical path length of the reference light beam L2, a beat signal that repetitively waxes and wanes at a difference frequency between the frequencies of the reference light beam L2 and the reflected light beam L3 is generated. As the optical path length of the reference light beam L2 is varied by the optical path length adjusting means 320, the measurement position (depth) within the measurement target S changes. The interference light detecting means 340 detects a plurality of beat signals at each measuring position. Note that data regarding the measuring positions is output to the image obtaining means 50 from the optical path adjusting means 320. Tomographic images are generated based on the beat signals detected by the interference light detecting means 340 and the data regarding the measuring positions from the mirror moving means 24. The display device 60 displays the generated tomographic images.

In the optical tomograph 300 of the third embodiment as well, the depolarizing means 70 is provided along the optical path of the reference light beam L2. Accordingly, the same advantageous effects as those obtained by the optical tomograph 100 of the first embodiment can be obtained. That is, an optical tomograph that obtains high quality tomographic images without adjusting the polarization directions of light beams can be obtained at low cost.

In the first through third embodiments described above, the depolarizing means 70 are provided along the optical path of the reference light beam L2. However, the present invention is not limited to this configuration, and the depolarizing means 70 may be provided in one or more of the following locations: within the light source unit; along the optical path of the light beam L between the light source unit and the light dividing means; along the optical path of the measuring light beam L1; along the optical path of the reference light beam L2; and along the optical path of the reflected light beam L3. Alternatively, the depolarizing means may be provided within the interior of the optical path length adjusting means.

Figure 4:
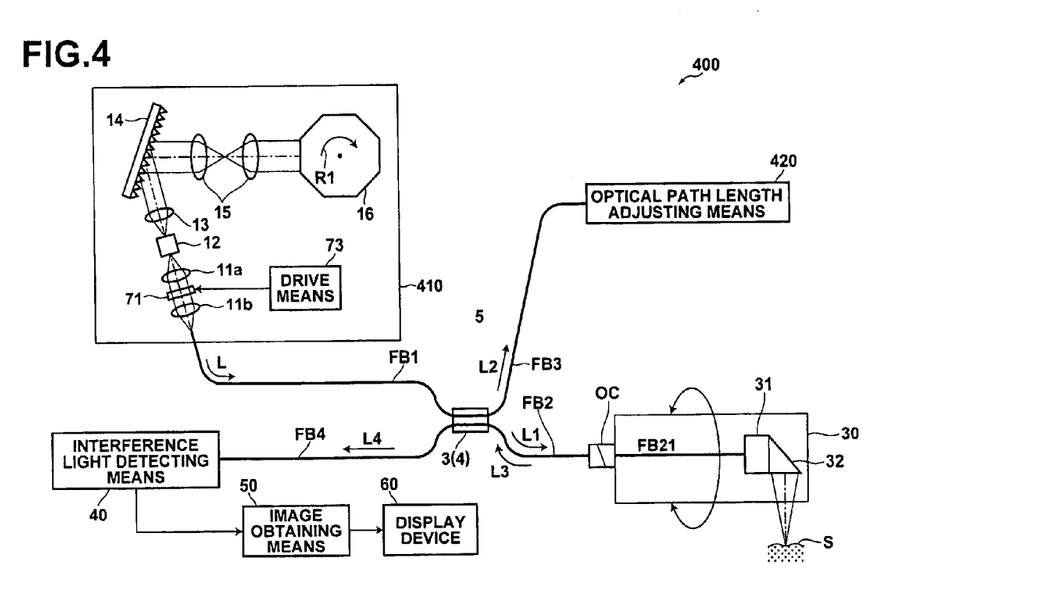
FIG. 4 is a diagram that illustrates the construction of an optical tomograph according to a fourth embodiment of the present invention.

Next, an optical tomograph 400 according to a fourth embodiment of the present invention will be described with reference to FIG. 4. Note that the optical tomograph 400 of the fourth embodiment obtains tomographic images by SS-OCT measurement, and differs from the optical tomograph 100 illustrated in FIG. 1 in that a depolarizing means is provided within a light source unit. Components of the optical tomograph 400 illustrated in FIG. 4 which are the same as those of the optical tomograph 100 illustrated in FIG. 1 will be denoted with the same reference numerals, and detailed descriptions thereof will be omitted.

The ½ wavelength plate 71 and the drive means 73 for rotating the ½ wavelength plate 71 are provided between the lens 1a and the lens 11b in a light source unit 410 of the optical tomograph 400. The ½ wavelength plate 71 and the drive means 73 constitute a depolarizing means. In the optical tomograph 400, the polarization states of both the measuring light beam L1 and the reference light beam L2 are enabled to be varied by the depolarizing means.

The depolarizing means is provided in the light source unit 410 of the optical tomograph 400. Accordingly, the need to form the optical path of the reference light beam L2 as a loop is obviated, and therefore a reflective type optical path length adjusting means 420 is employed. A combination of a collimating lens and a reflective mirror capable of moving in the direction of the optical axis of the reference light beam L2 maybe employed as the optical path length adjusting means 420.

Figure 5:
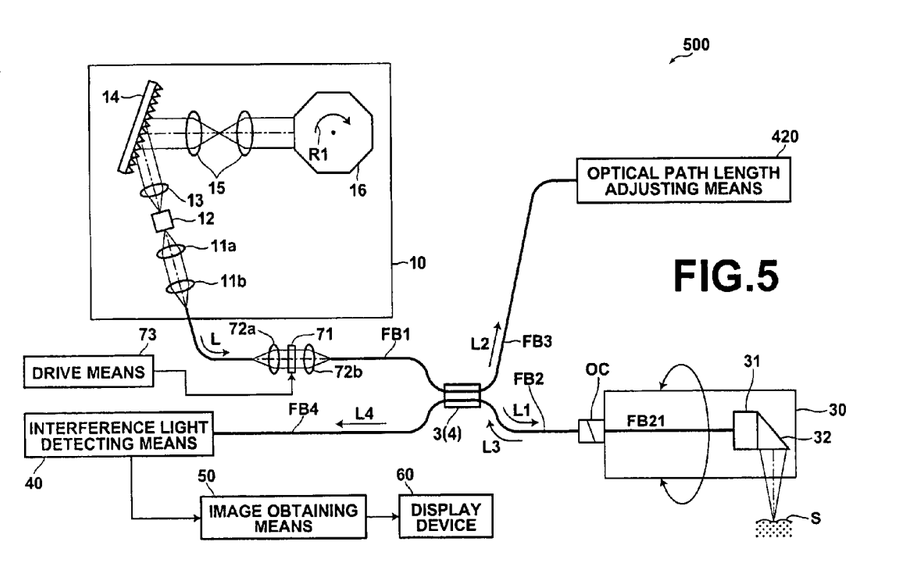
FIG. 5 is a diagram that illustrates the construction of an optical tomograph according to a fifth embodiment of the present invention.

Next, an optical tomograph 500 according to a fifth embodiment of the present invention will be described with reference to FIG. 5. Note that the optical tomograph 500 of the fifth embodiment obtains tomographic images by SS-OCT measurement, and differs from the optical tomograph 100 illustrated in FIG. 1 in that a depolarizing means is provided along the optical path of the light beam L. Components of the optical tomograph 500 illustrated in FIG. 5 which are the same as those of the optical tomograph 100 illustrated in FIG. 1 will be denoted with the same reference numerals, and detailed descriptions thereof will be omitted.

The optical tomograph 500 comprises: the ½ wavelength plate 71; the optical linking lenses 72a and 72b, each of which is provided on one side of the ½ wavelength plate 71 in the direction of the optical axis thereof; and the drive means 73, for rotating the ½ wavelength plate 72 about the optical axis of the light beam L. The ½ wavelength plate 71, the optical linking lenses 72a, 72b, and the drive means 73 constitute a depolarizing means.

In the optical tomograph 500 as well, the need to form the optical path of the reference light beam L2 as a loop is obviated, and therefore the reflective type optical path length adjusting means 420 is employed.

Note that the depolarizing means is not limited to those of the constructions described above. Alternate structures that constitute the depolarizing means will be described in the sixth through eighth embodiments below.

Figure 6:
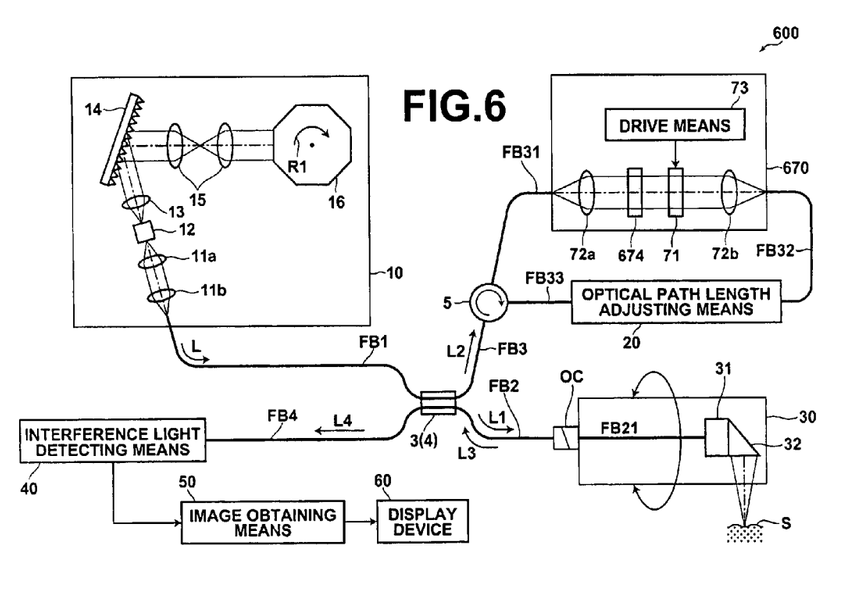
FIG. 6 is a diagram that illustrates the construction of an optical tomograph according to a sixth embodiment of the present invention.

Next, an optical tomograph 600 according to a sixth embodiment of the present invention will be described with reference to FIG. 6. Note that the optical tomograph 600 of the sixth embodiment differs from the optical tomograph 100 illustrated in FIG. 1 in the structure of the depolarizing means. Components of the optical tomograph 600 illustrated in FIG. 6 which are the same as those of the optical tomograph 100 illustrated in FIG. 1 will be denoted with the same reference numerals, and detailed descriptions thereof will be omitted.

A depolarizing means 670 of the optical tomograph 600 is of a structure in which a ¼ wavelength plate 674 is provided between the lens 72a and the ½ wavelength plate 71 of the depolarizing means 70 of FIG. 1. The ¼ wavelength plate 674 is provided to be coaxial with the ½ wavelength plate 71, and is fixed in the present embodiment.

The ¼ wavelength plate 674 is a birefringent plate that imparts a ¼ wavelength phase difference to linearly polarized light beams which are emitted perpendicular to each other. The ¼ wavelength plate 674 functions to convert a linearly polarized light beam incident thereon into a circularly polarized light beam, by setting a predetermined relationship between its polarizing axis and the polarization direction of the linearly polarized light beam.

Accordingly, in the case that a linearly polarized light beam is input to the depolarizing means 670, first, the light beam is converted into a circularly polarized light beam by the ¼ wavelength plate, then converted into a non polarized light beam when averaged over time, by the ½ wavelength plate 71 which is rotated at high speed. A single circularly polarized light beam may be considered as being separable into two linearly polarized light beams having perpendicular polarization directions. Therefore, the degree of depolarization imparted by the depolarizing means 670 is greater than that imparted by the depolarizing means 70.

Even if a single mode optical fiber is employed as a light guide, the polarized state of a light beam is maintained if the distance from the light source unit 10 to the depolarizing means 670 is short, and no great force is being applied to the optical fiber. It is considered that if a linearly polarized light beam is emitted by the light source unit 10, the light beam will enter the depolarizing means 670 while maintaining its linearly polarized state. Therefore, the optical tomograph 600 is of an effective structure in depolarizing the light beam.

Note that in the sixth embodiment, an example was described in which the ¼ wavelength plate 674 was employed. ⅛ wavelength plates and ⅝ wavelength plates are also capable of converting linearly polarized light beams into circularly polarized light beams. Therefore, wavelength plates that impart phase differences other than ¼ wavelengths may be employed as well.

In addition, the ¼ wavelength plate 674 of the optical tomograph 600 is fixed. Alternatively, the ¼ wavelength plate 674 may be rotated about the optical axis of the reference light beam L2 or vibrated. In this case, the speed at which the ¼ wavelength plate 674 is rotated or vibrated may be the same as that for the ½ wavelength plate 71, or different therefrom.

Figure 7:
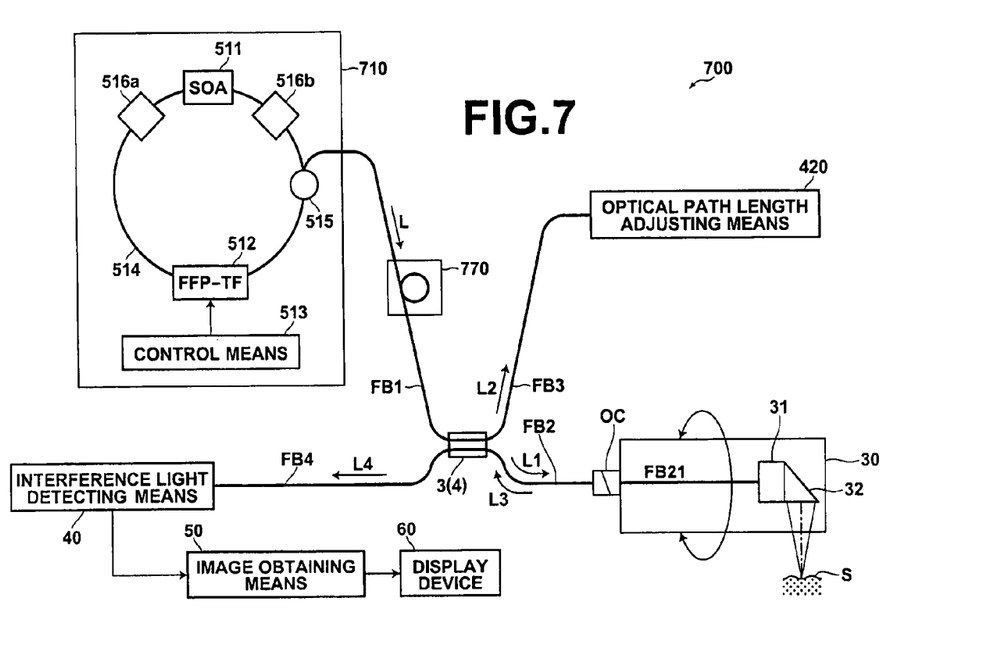
FIG. 7 is a diagram that illustrates the construction of an optical tomograph according to a seventh embodiment of the present invention.

Next, an optical tomograph 700 according to a seventh embodiment of the present invention will be described with reference to FIG. 7 and FIG. 8. A depolarizing means 770 is provided along the optical path of the light beam L emitted from a light source unit 710. However, the optical tomograph 700 of FIG. 7 differs from the optical tomograph 500 of FIG. 5 in the structure of the depolarizing means, and in the structure of the light source unit. Components of the optical tomograph 700 illustrated in FIG. 7 which are the same as those of the optical tomograph 500 illustrated in FIG. 5 will be denoted with the same reference numerals, and detailed descriptions thereof will be omitted.

Figure 8:
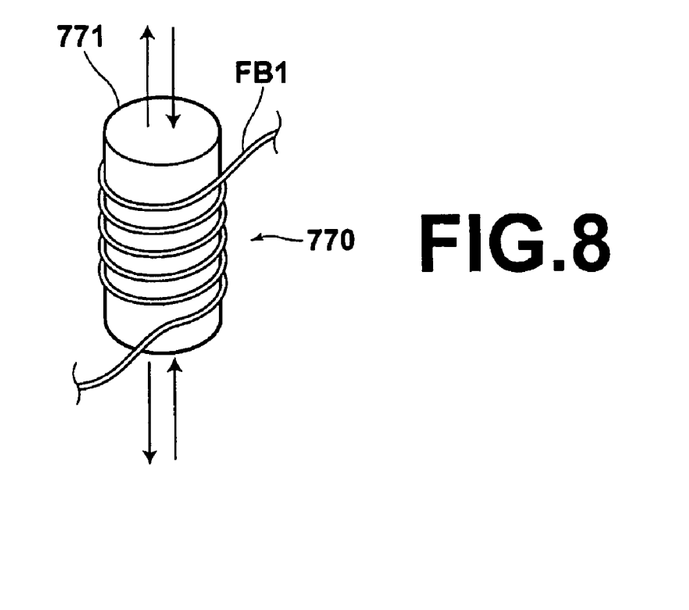
FIG. 8 is a diagram that illustrates the construction of a depolarizing means in the optical tomograph of FIG. 7.

FIG. 8 is a magnified view of a depolarizing means 770 of the optical tomograph 700. The depolarizing means 770 comprises: a portion of the optical fiber FB1 that constitutes the optical path of the light beam L, and an actuator 771, which is a force applying means for applying force onto the portion of the optical fiber FB1. The depolarizing means 770 is of a construction in which the portion of the optical fiber FB1 is wound about the periphery of the actuator 771, which is cylindrical. The actuator 771 may be constituted by a piezoelectric element, for example.

The actuator 771 is driven by a control means (not shown), to shrink and expand in the longitudinal direction thereof indicated by the arrows in FIG. 8. Force is applied to the optical fiber FB1 wound about the actuator 771 by the shrinkage and expansion thereof, the birifringent properties of the optical fiber FB1 changes due to the applied force, and the polarization state of the light beam L that propagates therethrough is varied. In this case as well, the actuator 771 is driven at a frequency equivalent to or higher than the scanning frequency. Note that it is preferable for the frequency at which the actuator 771 is driven to be equivalent to or higher than the wavelength sweeping frequency $f_\lambda$, and more preferably, equivalent to or higher than $N \times f_\lambda$.

Experiments were performed, in which 100 m of an optical fiber was wound about the outer periphery of a cylindrical actuator having a diameter of 20 mm, and the actuator was driven at drive frequencies of 1 kHz, 10 kHz, and 100 kHz. As a result, the polarization states of light beams that propagated through the optical fiber varied in a complex manner, and intensity changes at frequencies higher than the drive frequencies were observed in the interference light beam. It is estimated that the polarization states changed in such a complex manner within the optical fiber, because force was applied along the entire length of the 100 m long optical fiber. Density stripes within tomographic images obtained during these experiments were reduced compared to cases in which the depolarizing means 770 was not employed.

Note that the length of the fiber to be wound about the actuator is not limited to 100 m. The length of the fiber may be greater than 100 m, or less than 100 m, for example, 10 m. In the case that it is desired for the drive current for the actuator to be reduced, the length of the fiber may be lengthened, to obtain the depolarization effect. Alternatively, the length of the fiber may be shortened, depending on the design of the interferometer.

The light source unit 710 of the optical tomograph 700 comprises: an SOA 511 (Semiconductor Optical Amplifier); an FFP-TF 512 (Fiber Fabry Perot-Tunable Filter); a control means 513, for controlling the FFP-TF 512; an optical fiber FB514, which is connected to both ends of the SOA 511 and the FFP-TF 513, to form an ring shaped resonator; an optical fiber coupler 515, which is provided along the optical fiber FB514 and connected to the optical fiber FB1; and two isolators 516a and 516b, which are provided along the optical fiber FB514. The isolators 516a and 516b determine the direction that light propagates through the optical fiber FB514.

The SOA 511 outputs weak discharge light to the optical fiber which is connected to one end facet thereof when drive current is injected. The SOA 511 also functions to amplify light input from the optical fiber which is connected to the other end facet thereof. Due to these functions of the SOA 511, laser oscillation occurs within a ring shaped resonator formed by the optical fiber FB514. A portion of the laser beam is branched out by the optical fiber coupler 515, and is emitted toward the exterior of the light source unit 710 by the optical fiber FB1.

The FFP-TF 512 is a Fabry Perot type tunable filter, and only transmits light of a specific wavelength. The specific wavelength is set by the control means 513. The FFP-TF 512 and the control means 513 function as a wavelength selecting means. The wavelength selecting means enables selection of the wavelength of laser light that oscillates within the ring shaped resonator, and the light source unit 710 is enabled to sweep the wavelength of laser light emitted therefrom with a predetermined period.

Note that the light source unit 710 is not limited to be used in seventh embodiment, and may be applied to the optical tomographs 100, 400, 500, and 600 of the first and fourth through sixth embodiments as well. In addition, light source units to be utilized in SS-OCT measurement are not limited to those illustrated in FIGS. 1 and 7, and wavelength sweeping light source units having alternate constructions may be employed.

Figure 9:
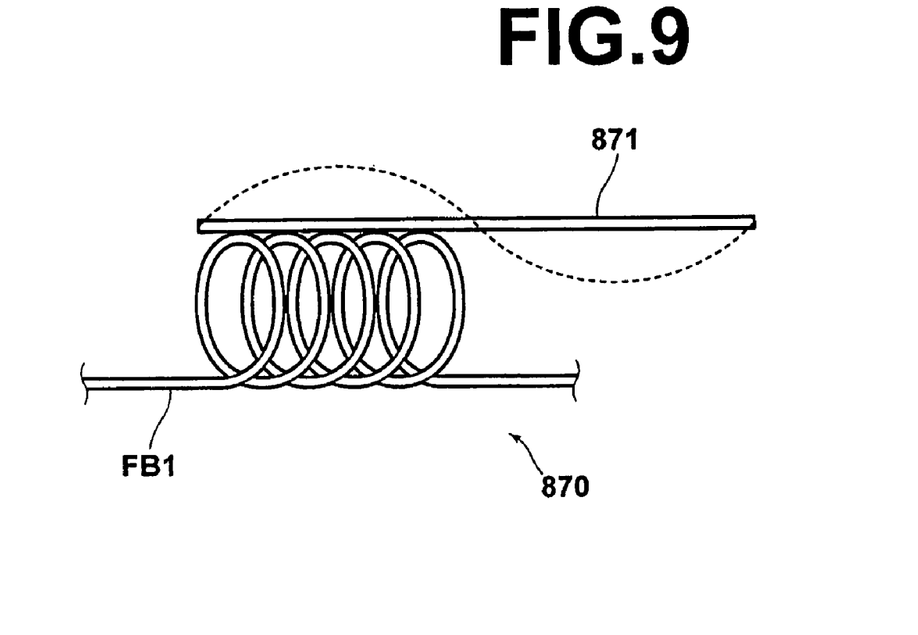
FIG. 9 is a diagram that illustrates the construction of a depolarizing means in an optical tomograph according to an eighth embodiment of the present invention.

Next, the eighth embodiment of the present invention will be described with reference to FIG. 9. The eight embodiment differs from the seventh embodiment only in the structure of the depolarizing means thereof. Therefore, a description will be given only regarding this point, and descriptions of the other components will be omitted.

A depolarizing means 870 employed in the eighth embodiment comprises: a portion of the optical fiber FB1, which is formed substantially into a coil; and a vibrating plate 871, for applying force to a portion of the outer periphery of the coiled optical fiber FB1. The vibrating plate 871 has a longitudinal direction which is substantially the same as the central axis of the coil formed by the optical fiber FB1, and is provided such that a first end thereof contacts the outer periphery of the coiled optical fiber FB1. A control means (not shown) drives a second end of the vibrating plate 871 to cause the entire vibrating plate 871 to vibrate. The vibration causes the vibrating plate 871 to apply force onto the optical fiber FB1. The preferred frequencies at which the vibrating plate 871 is caused to vibrate are the same as the drive frequencies of the seventh embodiment.

Preferred embodiments of the present invention have been described above. However, the present invention is not limited to the above embodiments, and various changes and modifications are possible, as long as they do not stray from the spirit of the invention.

For example, the depolarizing means of the optical tomograph is not limited to the examples described above, and various depolarizing means may be utilized. The depolarizing means may be a combination of various structures, such as a combination of that which utilizes a ½ wavelength plate and that which utilizes an actuator. Alternatively, the depolarizing means may be a combination of a plurality of similar structures. In the case that a plurality of structures are combined, it is preferable for the frequencies at which each structure varies the polarization state to be different from each other. In this case, density stripes in tomographic images can be reduced further.

Note that in the foregoing description, the first embodiment was an SS-OCT apparatus, and the second and third embodiments were an SD-OCT apparatus and a TD-OCT apparatus, to which the features of the first embodiment were applied. Similarly, the features of the fourth through eighth embodiments, may also be applied to SD-OCT apparatuses and TD-OCT apparatuses.

In addition, optical tomographs having constructions based on a Michelson interferometer were described in the above embodiments. Alternatively, other types of interferometers, such as a Mach Zehnder interferometer and a Fizeau interferometer, may be used.

What is claimed is:

1. An optical tomograph, comprising:
   a light source unit for emitting a light beam;
   light dividing means, for dividing the light beam emitted from the light source unit into a measuring light beam and a reference light beam;
   scanning means, for scanning and irradiating the measuring light beam onto a measurement target at a predetermined scanning frequency;
   combining means, for combining a reflected light beam, which is the measuring light beam reflected by the measurement target when scanned thereon, and the reference light beam;
   interference light detecting means, for detecting an interference light beam, which is formed by the reflected light beam and the reference light beam being combined by the combining means;
   image obtaining means, for detecting the intensity of the reflected light beam at a plurality of depth positions within the measurement target, based on the wavelength and intensity of the interference light beam detected by the interference light detecting means, and obtaining a tomographic image of the measurement target based on the intensities of the reflected light beam; and
   depolarizing means, for varying the polarization state of light beams input thereto at a frequency equivalent to or higher than the scanning frequency, such that the light beam output therefrom becomes depolarized when averaged over time, provided in at least one of the following locations: within the light source unit; along the optical path of the light beam emitted from the light source unit between the light source unit and the combining means; along the optical path of the measuring light beam; along the optical path of the reference light beam; and along the optical path of the reflected light beam.

2. An optical tomograph as defined in claim 1, wherein the depolarizing means comprises:
   a wavelength plate provided in the optical path of the light beam input into the depolarizing means; and
   drive means, for rotating the wavelength plate about the optical axis of the light beam.

3. An optical tomograph as defined in claim 1, wherein the depolarizing means comprises:
   a wavelength plate provided in the optical path of the light beam input into the depolarizing means; and
   drive means, for vibrating the wavelength plate.

4. An optical tomograph as defined in claim 1, wherein the depolarizing means comprises:
   an optical fiber that constitutes the optical path of at least one of the light beam emitted by the light source unit, the measuring light beam, the reference light beam, and the reflected light beam, between the light source unit and the combining means; and
   force applying means, for applying force on the optical fiber.

5. An optical tomograph as defined in claim 1, wherein:
   the light source unit emits a laser beam, of which the wavelength is swept with a predetermined sweeping frequency fλ;
   the image obtaining means obtains the tomographic image of the measurement target by administering spectral analysis on the interference light beam; and
   the depolarizing means varies the polarized state of the light beam input thereto at a frequency equivalent to or higher than the sweeping frequency fλ.

6. An optical tomograph as defined in claim 5, wherein the depolarizing means comprises:
   a wavelength plate provided in the optical path of the light beam input into the depolarizing means; and
   drive means, for rotating the wavelength plate about the optical axis of the light beam.

7. An optical tomograph as defined in claim 5, wherein the depolarizing means comprises:
   a wavelength plate provided in the optical path of the light beam input into the depolarizing means; and
   drive means, for vibrating the wavelength plate.

8. An optical tomograph as defined in claim 5, wherein the depolarizing means comprises:
   an optical fiber that constitutes the optical path of at least one of the light beam emitted by the light source unit, the measuring light beam, the reference light beam, and the reflected light beam, between the light source unit and the combining means; and
   force applying means, for applying force on the optical fiber.

9. An optical tomograph as defined in claim 5, wherein:
   the depolarizing means varies the polarized state of the light beam input thereto at a frequency equivalent to or higher than N fλ, wherein N is the number of depth positions at which the intensity of the reflected light beam is detected, and fλ is the frequency at which the wavelength of the laser beam is swept.

10. An optical tomograph as defined in claim 9, wherein the depolarizing means comprises:
    a wavelength plate provided in the optical path of the light beam input into the depolarizing means; and
    drive means, for rotating the wavelength plate about the optical axis of the light beam.

11. An optical tomograph as defined in claim 9, wherein the depolarizing means comprises:
    a wavelength plate provided in the optical path of the light beam input into the depolarizing means; and
    drive means, for vibrating the wavelength plate.

12. An optical tomograph as defined in claim 9, wherein the depolarizing means comprises:
- an optical fiber that constitutes the optical path of at least one of the light beam emitted by the light source unit, the measuring light beam, the reference light beam, and the reflected light beam, between the light source unit and the combining means; and
- force applying means, for applying force on the optical fiber.

13. An optical tomograph as defined in claim 1, wherein:
the light source unit emits low coherence light; and
the image obtaining means obtains the tomographic image of the measurement target by administering spectral analysis on the interference light beam.

14. An optical tomograph as defined in claim 13, wherein the depolarizing means comprises:
- a wavelength plate provided in the optical path of the light beam input into the depolarizing means; and
- drive means, for rotating the wavelength plate about the optical axis of the light beam.

15. An optical tomograph as defined in claim 13, wherein the depolarizing means comprises:
- a wavelength plate provided in the optical path of the light beam input into the depolarizing means; and
- drive means, for vibrating the wavelength plate.

16. An optical tomograph as defined in claim 13, wherein the depolarizing means comprises:
- an optical fiber that constitutes the optical path of at least one of the light beam emitted by the light source unit, the measuring light beam, the reference light beam, and the reflected light beam, between the light source unit and the combining means; and
- force applying means, for applying force on the optical fiber.

17. An optical tomograph as defined in claim 1, wherein:
the scanning means is equipped with optical fibers to guide the measuring light beam and the reflected light beam therethrough.

18. An optical tomograph as defined in claim 1, wherein:
the light source emits a laser beam, the wavelength of which is swept with a predetermined sweeping frequency;
the image obtaining means obtains the tomographic image of the measurement target by administering spectral analysis on the interference light beam; and
the scanning means comprises a probe, and the scanning frequency is a frequency at which the measuring light beam is polarized in the circumferential direction of the probe and scanned on the measurement target.

19. An optical tomograph, comprising:
a light source unit for emitting a light beam;
a light dividing section, for dividing the light beam emitted from the light source unit into a measuring light beam and a reference light beam;
a scanning section, for scanning and irradiating the measuring light beam onto a measurement target at a predetermined scanning frequency;
a combining section, for combining a reflected light beam, which is the measuring light beam reflected by the measurement target when scanned thereon, and the reference light beam;
an interference light detecting section, for detecting an interference light beam, which is formed by the reflected light beam and the reference light beam being combined by the combining section;
an image obtaining section, for detecting the intensity of the reflected light beam at a plurality of depth positions within the measurement target, based on the wavelength and intensity of the interference light beam detected by the interference light detecting section, and obtaining a tomographic image of the measurement target based on the intensities of the reflected light beam; and
a depolarizing section, provided in at least one of the following locations: within the light source unit; along the optical path of the light beam emitted from the light source unit between the light source unit and the combining means; along the optical path of the measuring light beam; along the optical path of the reference light beam; and along the optical path of the reflected light beam, for varying the polarization state of light beams input thereto at a frequency equivalent to or higher than the scanning frequency, such that the light beam output therefrom becomes depolarized when averaged over time.

\* \* \* \* \*